United States Patent
Burbank et al.

(10) Patent No.: US 11,783,939 B2
(45) Date of Patent: *Oct. 10, 2023

(54) SAFETY FEATURES FOR MEDICAL DEVICES REQUIRING ASSISTANCE AND SUPERVISION

(71) Applicant: NxStage Medical, Inc., Lawrence, MA (US)

(72) Inventors: Jeffrey H. Burbank, Manchester, MA (US); Dennis M. Treu, Castle Rock, CO (US); James M. Brugger, Newburyport, MA (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/139,442

(22) Filed: Dec. 31, 2020

(65) Prior Publication Data

US 2021/0125715 A1    Apr. 29, 2021

Related U.S. Application Data

(63) Continuation of application No. 15/977,619, filed on May 11, 2018, now abandoned, which is a
(Continued)

(51) Int. Cl.
*G08B 23/00* (2006.01)
*G16H 40/63* (2018.01)
(Continued)

(52) U.S. Cl.
CPC ........... *G16H 40/63* (2018.01); *A61B 5/0077* (2013.01); *A61B 5/015* (2013.01); *A61B 5/0816* (2013.01);
(Continued)

(58) Field of Classification Search
CPC ........ G16H 40/63; G16H 40/67; G16H 30/40; G16H 20/00; G16Z 99/00; A61B 5/0077;
(Continued)

(56) References Cited

U.S. PATENT DOCUMENTS 4,710,164 A    12/1987  Levin et al.
4,718,891 A    1/1988   Lipps
(Continued)

OTHER PUBLICATIONS

Srinivasan et al., A Wireless Continuous Patient Health Monitoring System Using IoT (Year: 2021).*
(Continued)

*Primary Examiner* — Quang Pham
(74) *Attorney, Agent, or Firm* — Potomac Law Group, PLLC

(57) ABSTRACT

An automatic monitoring system for a medical treatment device helps to ensure that an a medical treatment device operated at a treatment location away from a clinic is preformed safely. The monitoring system may verify that an assistant is present during treatment of the patient. Among the features disclosed biometric authentication to verify that a trained assistant is present, a presence detector to ensure the assistant is continuously present during treatment, and warning and recovery processes that allow intermittent lapses in the continuous presence of the assistant. The treatment device also communicates with a remote server or terminal.

18 Claims, 6 Drawing Sheets

Related U.S. Application Data continuation of application No. 15/189,532, filed on Jun. 22, 2016, now abandoned, which is a continuation of application No. 14/682,440, filed on Apr. 9, 2015, now Pat. No. 9,375,527, which is a continuation of application No. 13/618,716, filed on Sep. 14, 2012, now Pat. No. 9,024,746, which is a continuation of application No. 12/091,728, filed as application No. PCT/US2006/060218 on Oct. 25, 2006, now abandoned.

(60) Provisional application No. 60/596,840, filed on Oct. 25, 2005.

(51) Int. Cl.

| | | |
|---|---|---|
| A61M 1/14 | (2006.01) | |
| A61M 1/36 | (2006.01) | |
| A61B 5/117 | (2016.01) | |
| A61B 5/00 | (2006.01) | |
| G16H 40/67 | (2018.01) | |
| G16H 30/40 | (2018.01) | |
| G16Z 99/00 | (2019.01) | |
| G05B 1/01 | (2006.01) | |
| G05B 9/02 | (2006.01) | |
| G08B 21/22 | (2006.01) | |
| A61B 5/01 | (2006.01) | |
| A61B 5/08 | (2006.01) | |
| G08B 21/18 | (2006.01) | |
| G16H 20/00 | (2018.01) | |

(52) U.S. Cl.
CPC .............. *A61B 5/117* (2013.01); *A61B 5/746* (2013.01); *A61B 5/7475* (2013.01); *A61M 1/14* (2013.01); *A61M 1/36* (2013.01); *A61M 1/367* (2013.01); *G05B 1/01* (2013.01); *G05B 9/02* (2013.01); *G08B 21/182* (2013.01); *G08B 21/22* (2013.01); *G16H 30/40* (2018.01); *G16H 40/67* (2018.01); *G16Z 99/00* (2019.02); *A61M 2205/18* (2013.01); *A61M 2205/3553* (2013.01); *A61M 2205/6009* (2013.01); *G16H 20/00* (2018.01)

(58) Field of Classification Search
CPC ....... A61B 5/015; A61B 5/0816; A61B 5/117; A61B 5/746; A61B 5/7475; A61M 1/14; A61M 1/36; A61M 1/367; A61M 2205/18; A61M 2205/3553; A61M 2205/6009; G05B 1/01; G05B 9/02; G08B 21/182; G08B 21/22
See application file for complete search history.

(56) References Cited

U.S. PATENT DOCUMENTS

| | | | |
|---|---|---|---|
| 4,885,571 A * | 12/1989 | Pauley | G06K 19/07749 455/100 |
| 5,104,374 A | 4/1992 | Bishko et al. | |
| 5,218,344 A * | 6/1993 | Ricketts | G08B 25/016 379/38 |
| 5,232,439 A | 8/1993 | Campbell et al. | |
| 5,507,277 A | 4/1996 | Rubsamen et al. | |
| 5,531,697 A | 7/1996 | Olsen et al. | |
| 5,561,718 A | 10/1996 | Trew et al. | |
| 5,905,602 A * | 5/1999 | Pak | G11B 27/007 |
| 5,984,175 A | 11/1999 | Popp | |
| 6,026,684 A | 2/2000 | Calder | |
| 6,039,251 A * | 3/2000 | Holowko | A61M 5/172 235/380 |
| 6,183,412 B1 | 2/2001 | Benkowski et al. | |
| 6,297,738 B1 * | 10/2001 | Newham | G08B 21/22 340/568.1 |
| 6,359,557 B2 | 3/2002 | Bilder | |
| 6,515,575 B1 | 2/2003 | Kataoka | |
| 6,594,524 B2 | 7/2003 | Esteller | |
| 6,611,206 B2 | 8/2003 | Eshelman et al. | |
| 6,611,914 B1 * | 8/2003 | Lee | G06F 21/83 709/224 |
| 6,615,356 B1 | 9/2003 | Byun | |
| 6,699,195 B2 | 3/2004 | Nakazawa et al. | |
| 6,714,594 B2 | 3/2004 | Dimitrova et al. | |
| 6,717,518 B1 | 4/2004 | Pirim et al. | |
| 6,717,957 B1 * | 4/2004 | Quine | H04L 67/55 709/219 |
| 6,766,456 B1 | 7/2004 | McKeeth | |
| 6,778,705 B2 | 8/2004 | Gulla et al. | |
| 6,782,415 B1 * | 8/2004 | Quine | G06Q 10/107 709/206 |
| 6,796,799 B1 | 9/2004 | Yoshiike et al. | |
| 6,796,955 B2 * | 9/2004 | O'Mahony | A61M 1/3656 210/651 |
| 6,889,074 B2 | 5/2005 | Uber et al. | |
| 6,920,360 B2 * | 7/2005 | Lee | A61N 1/37282 607/30 |
| 6,925,197 B2 | 8/2005 | Dimitrova et al. | |
| 6,931,596 B2 | 8/2005 | Gutta et al. | |
| 6,993,658 B1 * | 1/2006 | Engberg | G06F 21/43 379/114.2 |
| 7,028,269 B1 | 4/2006 | Cohen-Solal et al. | |
| 7,110,569 B2 | 9/2006 | Brodsky et al. | |
| 7,110,570 B1 | 9/2006 | Berenz et al. | |
| 7,236,936 B2 | 6/2007 | White et al. | |
| 7,522,057 B2 * | 4/2009 | Stern | G08B 21/0476 340/568.1 |
| 7,539,724 B1 * | 5/2009 | Callaghan | H04L 12/1822 709/205 |
| 7,706,896 B2 | 4/2010 | Music et al. | |
| 7,734,476 B2 * | 6/2010 | Wildman | G16H 40/20 705/2 |
| 7,742,821 B1 * | 6/2010 | Vamos | A61N 1/37217 607/60 |
| 7,780,618 B2 | 8/2010 | Felt et al. | |
| 7,925,063 B2 | 4/2011 | Ishida et al. | |
| 7,933,780 B2 * | 4/2011 | De La Huerga | A61M 5/16827 705/2 |
| 7,965,171 B2 | 6/2011 | Hershkovitz | |
| 8,006,099 B2 | 8/2011 | Aoyama et al. | |
| 8,143,994 B2 | 3/2012 | Jung | |
| 8,402,141 B2 | 3/2013 | Seraphin | |
| 8,954,336 B2 * | 2/2015 | Blomquist | G16H 40/63 705/2 |
| 9,864,839 B2 | 1/2018 | Baym et al. | |
| 10,232,103 B1 * | 3/2019 | Karoor | A61M 1/284 |
| 10,792,414 B2 * | 10/2020 | Updyke | A61M 1/1621 |
| 2001/0012917 A1 | 8/2001 | Inukai et al. | |
| 2001/0016696 A1 * | 8/2001 | Bystrom | A61H 31/005 601/41 |
| 2001/0037056 A1 | 11/2001 | Nunome | |
| 2002/0010679 A1 | 1/2002 | Felsher | |
| 2002/0038392 A1 * | 3/2002 | De La Huerga | G16H 20/17 710/8 |
| 2002/0049916 A1 | 4/2002 | Nozaki | |
| 2002/0067258 A1 | 6/2002 | Lyons et al. | |
| 2002/0069030 A1 * | 6/2002 | Xydis | G06F 21/35 702/176 |
| 2002/0082480 A1 | 6/2002 | Riff et al. | |
| 2002/0103674 A1 * | 8/2002 | Reeder | G08B 25/008 705/3 |
| 2002/0147423 A1 * | 10/2002 | Burbank | A61M 1/34 604/4.01 |
| 2002/0167408 A1 | 11/2002 | Trajkovic et al. | |
| 2002/0169635 A1 | 11/2002 | Shillingburg | |
| 2002/0173696 A1 | 11/2002 | Kolarovic et al. | |
| 2002/0196274 A1 * | 12/2002 | Comfort | G06F 21/31 715/741 |
| 2003/0001743 A1 | 1/2003 | Menard | |
| 2003/0025602 A1 | 2/2003 | Medema et al. | |

(56) References Cited

U.S. PATENT DOCUMENTS

| | | | |
|---|---|---|---|
| 2003/0055321 A1 | 3/2003 | Watrous et al. | |
| 2003/0079746 A1 | 5/2003 | Hickle | |
| 2003/0080850 A1* | 5/2003 | Kline | G07C 9/28 340/5.6 |
| 2003/0128125 A1* | 7/2003 | Burbank | G01M 3/26 340/605 |
| 2003/0128126 A1 | 7/2003 | Burbank et al. | |
| 2003/0138349 A1 | 7/2003 | Robinson et al. | |
| 2003/0152482 A1* | 8/2003 | O'Mahony | A61M 1/3656 422/44 |
| 2003/0172940 A1* | 9/2003 | Rogers | A61N 1/08 128/899 |
| 2004/0034810 A1* | 2/2004 | Heckmann | G06F 11/3006 714/11 |
| 2004/0143677 A1* | 7/2004 | Novak | G16H 40/63 600/300 |
| 2004/0167465 A1* | 8/2004 | Mihai | A61B 5/411 604/67 |
| 2004/0172301 A1* | 9/2004 | Mihai | A61B 5/0002 705/2 |
| 2004/0199408 A1 | 10/2004 | Johnson | |
| 2004/0199769 A1 | 10/2004 | Proudler | |
| 2004/0230811 A1 | 11/2004 | Siegel et al. | |
| 2004/0243046 A1 | 12/2004 | Brugger et al. | |
| 2005/0004502 A1 | 1/2005 | O'Mahony et al. | |
| 2005/0055244 A1 | 3/2005 | Mullan et al. | |
| 2005/0065817 A1* | 3/2005 | Mihai | A61B 5/411 705/2 |
| 2005/0080326 A1 | 4/2005 | Mathew | |
| 2005/0085760 A1* | 4/2005 | Ware | A61M 1/3437 604/4.01 |
| 2005/0102167 A1* | 5/2005 | Kapoor | G16H 40/20 705/3 |
| 2005/0107689 A1 | 5/2005 | Sasano | |
| 2005/0109333 A1* | 5/2005 | Thomas | F24C 7/082 126/42 |
| 2005/0119597 A1* | 6/2005 | O'Mahony | A61M 25/0028 604/4.01 |
| 2005/0131740 A1 | 6/2005 | Massenzio et al. | |
| 2005/0137653 A1* | 6/2005 | Friedman | H04L 67/12 607/60 |
| 2005/0137827 A1* | 6/2005 | Takamiya | G01S 5/30 702/150 |
| 2005/0159985 A1 | 7/2005 | Bertram | |
| 2005/0165626 A1* | 7/2005 | Karpf | G06Q 10/10 705/3 |
| 2005/0196023 A1 | 9/2005 | Chen et al. | |
| 2005/0200486 A1* | 9/2005 | Greer | G16H 40/40 340/573.1 |
| 2005/0212658 A1 | 9/2005 | Kinsella | |
| 2005/0234381 A1 | 10/2005 | Niemetz et al. | |
| 2005/0240305 A1* | 10/2005 | Bogash | G07F 11/68 700/242 |
| 2005/0261942 A1 | 11/2005 | Wheeler | |
| 2005/0270140 A1 | 12/2005 | Oh | |
| 2005/0277890 A1 | 12/2005 | Stewart et al. | |
| 2005/0283198 A1 | 12/2005 | Haubrich et al. | |
| 2005/0288572 A1 | 12/2005 | Graw | |
| 2006/0030891 A1* | 2/2006 | Saltzstein | H04W 84/022 607/32 |
| 2006/0092455 A1 | 5/2006 | Maeda et al. | |
| 2006/0105751 A1* | 5/2006 | Bloom | G07F 7/1008 455/412.2 |
| 2006/0122863 A1 | 6/2006 | Gottesman et al. | |
| 2006/0132283 A1 | 6/2006 | Eberhart et al. | |
| 2006/0138915 A1 | 6/2006 | Goldberg | |
| 2006/0155389 A1 | 7/2006 | Pessolano et al. | |
| 2006/0156028 A1 | 7/2006 | Aoyama et al. | |
| 2006/0181424 A1 | 8/2006 | Graves et al. | |
| 2006/0204050 A1 | 9/2006 | Takizawa | |
| 2006/0210112 A1 | 9/2006 | Cohen et al. | |
| 2006/0210958 A1 | 9/2006 | Rimas-Ribikauskas et al. | |
| 2006/0294390 A1 | 12/2006 | Navratil et al. | |
| 2007/0021981 A1 | 1/2007 | Cox | |
| 2007/0055888 A1 | 3/2007 | Miller et al. | |
| 2007/0088664 A1 | 4/2007 | Nakano et al. | |
| 2007/0174099 A1 | 7/2007 | Ostroscki et al. | |
| 2007/0180047 A1 | 8/2007 | Dong et al. | |
| 2007/0185615 A1 | 8/2007 | Bossi et al. | |
| 2007/0209063 A1 | 9/2007 | Ohto | |
| 2008/0053905 A9 | 3/2008 | Brugger et al. | |
| 2008/0055039 A1 | 3/2008 | Eberhart et al. | |
| 2008/0059228 A1 | 3/2008 | Bossi et al. | |
| 2008/0143538 A1 | 6/2008 | Young et al. | |
| 2009/0012472 A1* | 1/2009 | Ahm | A61M 5/158 604/138 |
| 2009/0037715 A1 | 2/2009 | Ali et al. | |
| 2009/0219131 A1 | 9/2009 | Barnett et al. | |
| 2009/0275807 A1 | 11/2009 | Sitzman et al. | |
| 2018/0184971 A1 | 7/2018 | Hong | |
| 2020/0111341 A1* | 4/2020 | Zhao | G06V 40/23 |
| 2021/0073545 A1* | 3/2021 | Buchaca | G06V 10/82 |
| 2021/0125715 A1* | 4/2021 | Burbank | G08B 21/182 |

OTHER PUBLICATIONS

Suarez-Coloma et al., Personalized temporal medical alert system (Year: 2013).*

\* cited by examiner

SAFETY FEATURES FOR MEDICAL DEVICES REQUIRING ASSISTANCE AND SUPERVISION

CROSS-REFERENCE TO RELATED APPLICATIONS

The present application is a continuation of U.S. patent application Ser. No. 15/977,619 filed on May 11, 2018, which is a continuation of U.S. patent application Ser. No. 15/189,532 filed Jun. 22, 2016, which is a continuation of U.S. patent application Ser. No. 14/682,440 filed Apr. 9, 2015, now U.S. Pat. No. 9,375,527 issued Jun. 28, 2016, which is a continuation of U.S. patent application Ser. No. 13/618,716 filed Sep. 14, 2012, now U.S. Pat. No. 9,024,746 issued May 5, 2015, which is a continuation of U.S. patent application Ser. No. 12/091,728 filed Aug. 19, 2008, abandoned, which is a national stage entry of International Application No. PCT/US2006/060218 filed Oct. 25, 2006, which claims the benefit of priority of U.S. Provisional Patent Application No. 60/596,840 filed Oct. 25, 2005, all of which are incorporated herein by reference in their entireties.

BACKGROUND

Home treatment can provide tremendous benefits for sufferers of chronic ailments such as renal failure. But there is potential for harm in the home setting that is offset in a clinical setting by the presence of trained staff. If a patient undergoing dialysis, for example, has a reaction due to unforeseen conditions, the staff can take immediate action to assist the patient, even if the patient loses consciousness. In the home, this role may be played by a trained assistant. The instructions and training associated with home use may be replete with admonitions against attempting to perform a treatment without following the requirement that the assistant be in attendance, but there is always a need for creative approaches that further help to ensure that such requirements are fulfilled.

SUMMARY

A home treatment system includes various devices to limit the potential for a patient to misuse a home medical treatment device or its components by limiting access to or use of equipment while not attended by an assistant or other authorized party.

According to an embodiment, a method verifies proper use of a medical device. The method includes authenticating an authorized person other than a patient to be treated using a device attached to a treatment device used to treat the patient, generating an enabling signal to cause the treatment device to become operable in response to a result of the step of authenticating, verifying at least one time during a treatment interval that an individual other than the patient is at a treatment location where the patient and the treatment device are located, performing a warning procedure responsively to a result of the step of verifying. The warning procedure includes generating a signal to indicate an impending termination of treatment within a specified time. The method further includes waiting for the individual to verify a presence of the individual within the specified time and terminating a treatment of the patient responsively to and after the step of waiting.

In a further embodiment, the authenticating includes machine-recognizing a biometric indicator of identity. The warning procedure may include displaying requirements for a treatment procedure, a message requesting the presence of the authorized person, a message transmission to a remote terminal such as a cell phone, a remote networked terminal (such as at a medical center), or a land line telephone. The authenticating may include reading a magnetic medium storing a data key, a finger, retina, keypad entry, RFID tag, the receiving of a mechanical key, or any suitable authentication process.

In a particular embodiment, the authenticating includes machine-classification of a video image such as recognizing the face of an assistant. Video classification is particularly useful in this context because it allows the treatment scene to be assessed in a variety of ways. For example, a video scene can be classified to determine if a person other than the patient remains with the patient during the treatment. The video system can "watch" the scene to make sure that if the helper does leave for a period of time, it is only for a predefined interval. A model of the treatment scene can be predefined as part of the classification process. For example, the model may specify that the helper will prepare a meal at a particular time or that the helper uses the bathroom with a predefined frequency. Thus, the model may be identified as storing a "pattern of presences of the helper." The model can be programmed specifically for this purpose or it can be acquired passively by observing behavior. By comparing consistency with the model (or in the case of the passively acquired model, this amounts to consistency from treatment to treatment) the video recognition system can determine if the non-presence of a helper is out of an expected bound. For example, if the model indicates that the helper should leave approximately at noon for 15 minutes and the helper leaves for 30 minutes, the system may initiate the protective features described in this application, such as sounding an annunciator or displaying a message to try to call back the helper or, upon failing that, the system may go into a failsafe mode. A video system even can have the ability to determine if the helper has fallen asleep by observing posture and movement of the helper.

Preferably, the method further includes authenticating an authorized person at least three times during a treatment interval, the three times being spaced apart such that the third time is more than half-way through the treatment interval. Even more preferably, the system continuously monitors indicia of the presence of the helper.

A medical device, comprising: controls for operating the medical device; a lock that prevents at least some functions of medical device from being operable through the controls; the lock granting initial access to the medical when a key is applied to the lock; a message generator that indicates that the medical device will go into a failsafe mode unless the lock is applied again at at least one time during a treatment interval; the lock permitting continued operation of the in response to the key being applied at the at least one time; the medical device being configured to go into the failsafe mode when the key is not applied during the at least one time.

The lock may be configured to perform machine-recognition of a biometric indicator of identity. The device may include a display and a message generator that displays on the display requirements for a treatment procedure. The device may also have a communication device including one of a wireless terminal, a telephone, and a networked terminal that generates a message indicating the failure of the key to be applied to the lock at the at least one time. The key may include a magnetic medium storing a data key. The lock may include a video camera and a device configured for machine-classification of a video image from the video camera. The lock may be a simple structure, for example one that prevent access by locking an access panel covering the controls.

Note that here and elsewhere in the specification, the term "video image" can also refer to a video stream or sequence of images or a metric derived from it. For example, an activity level in a scene can be determined from a compression metric such as MPEG motion compensation vector, or the average total energy in the motion compensation vector over a period of time. This would also fall under the meaning of "video image."

According to another embodiment, a medical device, has a medical treatment component and a monitoring system configured to receive data from sensors to confirm the presence of a helper. The helper is different from a patient receiving treatment by the medical treatment component. The monitoring system is configured to confirm a pattern of presences of the helper during a treatment period in which the medical treatment component is operative to deliver therapy to a patient. The monitoring system generates a signal indicative of an abnormal condition when the pattern of presences of the helper is not confirmed.

The monitoring system can include a video camera and a video classification engine that monitors a scene that includes a patient and a helper. In this embodiment, the monitoring system may initially authenticate the helper using any of a variety of known techniques, such as fingerprint identification. This process may also include machine-classification of a video image such as recognizing the face of the helper. Video classification is particularly useful in this context because it allows the treatment scene to be assessed in a variety of ways and continually monitored. For example, a video scene can be classified to determine if a person other than the patient remains with the patient during the treatment. The video system can "watch'" the scene to make sure that if the helper does leave for a period of time, it is only for a predefined interval. A model of the treatment scene can be predefined as part of the classification process. For example, the model may specify that the helper will prepare a meal at a particular time or that the helper uses the bathroom with a predefined frequency. Thus, the model may be identified as storing a "pattern of presences of the helper." The model can be programmed specifically for this purpose or it can be acquired passively by observing behavior. By comparing consistency with the model (or in the case of the passively acquired model this amounts to consistency from treatment to treatment) the video recognition system can determine if the non-presence of a helper is out of an expected bound. For example, if the model indicates that the helper should leave approximately at noon for 15 minutes and the helper leaves tor 30 minutes, the system may initiate the protective features described in this application, such as sounding an annunciator or displaying a message to try to call back the helper or, upon failing that, the system may go into a failsafe mode. A video system even can have the ability to determine if the helper has fallen asleep by observing posture and movement of the helper.

The sensors in this embodiment, instead of being a video camera (or in addition to a video camera and recognition engine) can also include components that are much simpler such as a pressure sensor in a chair or a proximity sensor which responds to the presence of the helper near or on the sensor. The sensor may be a keypad the prompts the helper to enter a code that indicates that helper is present and there are no problems with the treatment. The ability of the keypad entry to be made confirms the helper is available. Preferably, the helper would know the keycode for entry into the keypad but the patient would not. In this way the presence of the helper can be confirmed quite simply.

The authentication device or the presence indicator or sensor may include at least one of a key code receiver, an RFID reader, a mechanical lock, a biometric reader, a mag stripe reader, a non-volatile memory card reader, a smart card reader, a video camera, or a bar code reader. The monitoring system may go into a failsafe mode in response to the abnormal condition signal. The monitoring system may cause the medical treatment component to go into a failsafe mode in response to the abnormal condition signal. The monitoring system can generate an alert signal in response to the abnormal condition signal. It may wait for the reception of an alert-cancel command after generating the alert signal in which case it would reset and continue normal treatment operation of the medical treatment component. But if the alert-cancel command was not received, the monitoring system would cause the medical treatment component to go into a failsafe mode.

The failsafe mode of the present and other embodiments may include clamping blood lines and/or sending remote alerts such as a phone call to an ambulance service or 24 hour medical treatment facility. It may include the slowing of the blood pumping rate. The failsafe mode may be any operational mode that reduces the risk to the patient for any of the problems that can arise in a treatment. In a preferred embodiment, the features described in the present patent specification are applied to a renal replacement therapy system and/or a extracorporeal blood treatment.

DETAILED DESCRIPTION OF THE FIGURES

Figure 1A:
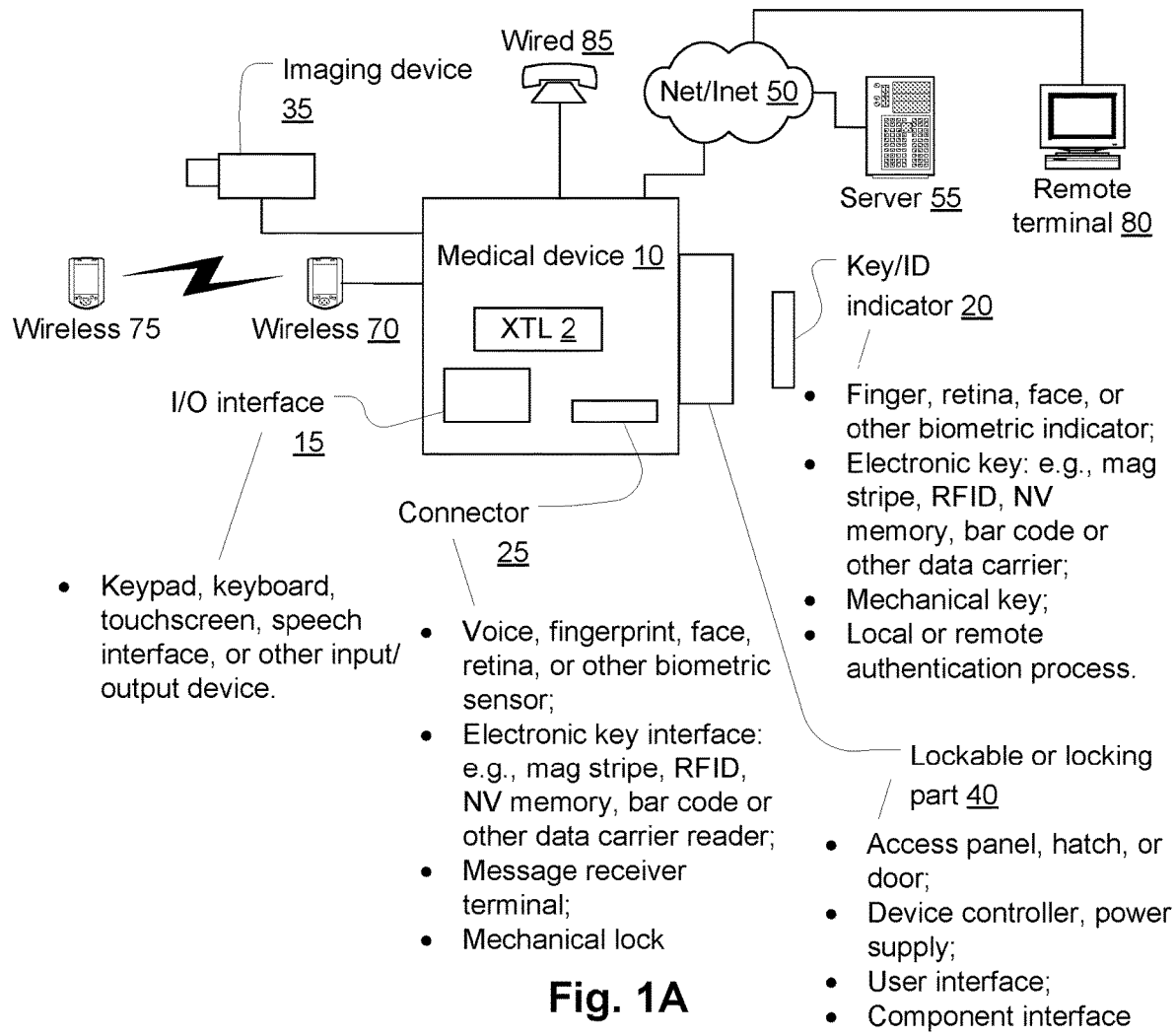
FIG. 1A is an illustration of an interface environment that supports various inventive embodiments.

Referring to FIG. 1A, a medical device 10 may have a controller 2 that controls the functions of the medical device 10. Examples of medical device 10 include renal replacement therapy, infusion pumps and associated systems; medical monitoring equipment, medicating systems, exercise equipment, physical therapy equipment, pulmonary treatment devices such as for chronic obstructive pulmonary disease, oxygen delivery systems, cardiac treatment or monitoring devices, and many others that may be evident to those of ordinary skill based on the current disclosure.

The medical device 10 may have a movable or stationary locking or lockable part 40 that is susceptible to locking or effects a locked and/or unlocked state. For example, it may be a part that is locked or a device, such as an actuator, that actually effects locking. Examples include solenoids, simple mechanical locks, software state machines with locked states through which operational flow is blocked, and other equivalent devices.

The controller 2 may implement a locking function or the entire medical device 10 may be susceptible to locking. Examples of a lockable part 30 include an access panel, hatch, door or other mechanical security component or mechanical interface such as a slot for receiving consumable components; a component controller, power supply, or a crucial component such as a pump or other prime mover; a user interface or component interface. The lockable part 40 may or may not be physically attached to the medical device 10. Its operative relationship with the medical device 10 and other elements, however, will become clearer from the greater disclosure.

The Medical device 10 may have one or more of a variety of communications and input and output elements, including:

A wireless terminal 70 to communicate with remote wireless terminals 75 such as cell phones, email devices, telemetry systems, wireless computer terminals, and similar devices. The medical device 10 may, for example, transmit information and receive commands via such devices.

An imaging device 35 such as a charge coupled device (CCD) video camera, laser scanner such as an industrial photometric scanner, an infrared camera, terahertz wave (T-wave) shortwave, acoustic, or other kind of imaging device. The medical device 10 may employ video image processing and recognition techniques to identify faces, determine the number of individuals present in a room, patient body surface temperature profile, or myriad other functions using the one or more imaging devices represented by imaging device 35.

A wired terminal 85 such as a plain old telephone (POT), annunciator such as an audible or visual alarm, intercom, or similar device. The medical device 10 may employ the wired terminal 85 to notify local or remote personnel of status or change of status at a treatment site. For example, the device 10 may place an automatic phone call to emergency medical personnel if predefined conditions are detected. The medical device 10 may also report attempts to authorize a treatment (see further below for discussion of this) or an attempt to use the medical device 10 to an authorized party with supervisory obligations.

The treatment device 10 (or a component thereof) may be connected to a network or the Internet 54 to communicate with information servers 55 and/or remote terminals 80. The medical device may use this capability to obtain instructions from the server 56, to report status or notify of conditions requiring special or immediate attention, and similar transactions. The medical device 10 may also use such communication modes to report attempts to authorize a treatment (see further below for discussion of this) or an attempt to use the medical device 10 to an authorized party with supervisory obligations.

A direct input/output (I/O) interface 15 such as a keyboard, keypad, speech interface, digital display, touchscreen, touchpad, or other I/O device and mechanical interface such as levers, buttons, knobs, etc. One or more such devices may be used to allow users or others to command and control the medical device 10 and/or the controller 2.

A connector 25 such as a port (e.g., USB port), mechanical keyhole, smart card reader, bar-code reader, mag-stripe reader, RFID reader, biometric sensor, handwriting recognition interface, or other interface device, which may be used for authorizing and/or authenticating a user and/or assistant.

A key or identification indicator represented figuratively at 20. These may include a human finger (fingerprint), retina, face, or other biometric indicator; an electronic key such as a magnetic stripe, radio frequency identification device (RFID) unit, nonvolatile memory (NV memory), bar code or other data carrier; mechanical key; or any device used in a remote or local authorization or authentication process. Another example is a key fob with a password or digital key embedded in a memory and a USB connector on it.

The above examples are by no means intended as an exhaustive list and are considered to encompass their equivalents and additional examples within the identified categories.

Figure 1B:
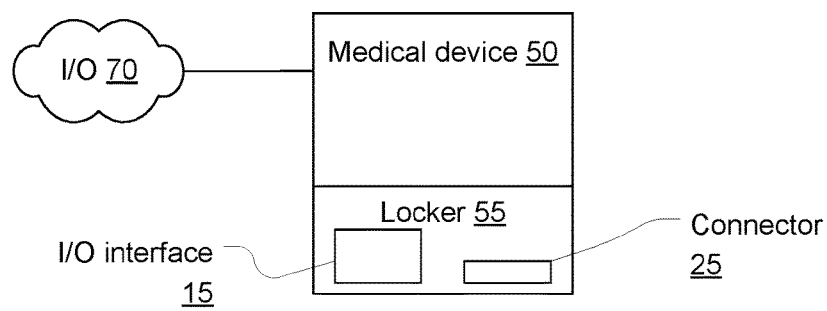
FIG. 1B illustrates an embodiment of a locking cabinet used to store components used for treatment.

In an alternative embodiment, shown in FIG. 1B, a locker 55 is provided to contain components that are used with the medical device 50 such that their inaccessibility reduces the ability of someone without access to the locker 55 to harm himself or another. Cloud 70 is intended to represent any or more of the input and output elements discussed and illustrated with reference to FIG. 1A. An example of the use of the locker would be as a store to hold consumables such as needle accesses or disposable blood circuits without which the medical device 50 could not be employed. The embodiment of FIG. 1B has the additional benefit of mitigating any risks from harm from the locked-up components themselves with or without the medical device 50. In the embodiment of FIG. 1B, the locker 55 may include substantially the same I/O Interface and/or connector 25 as discussed with reference to FIG. 1A.

Figure 2:
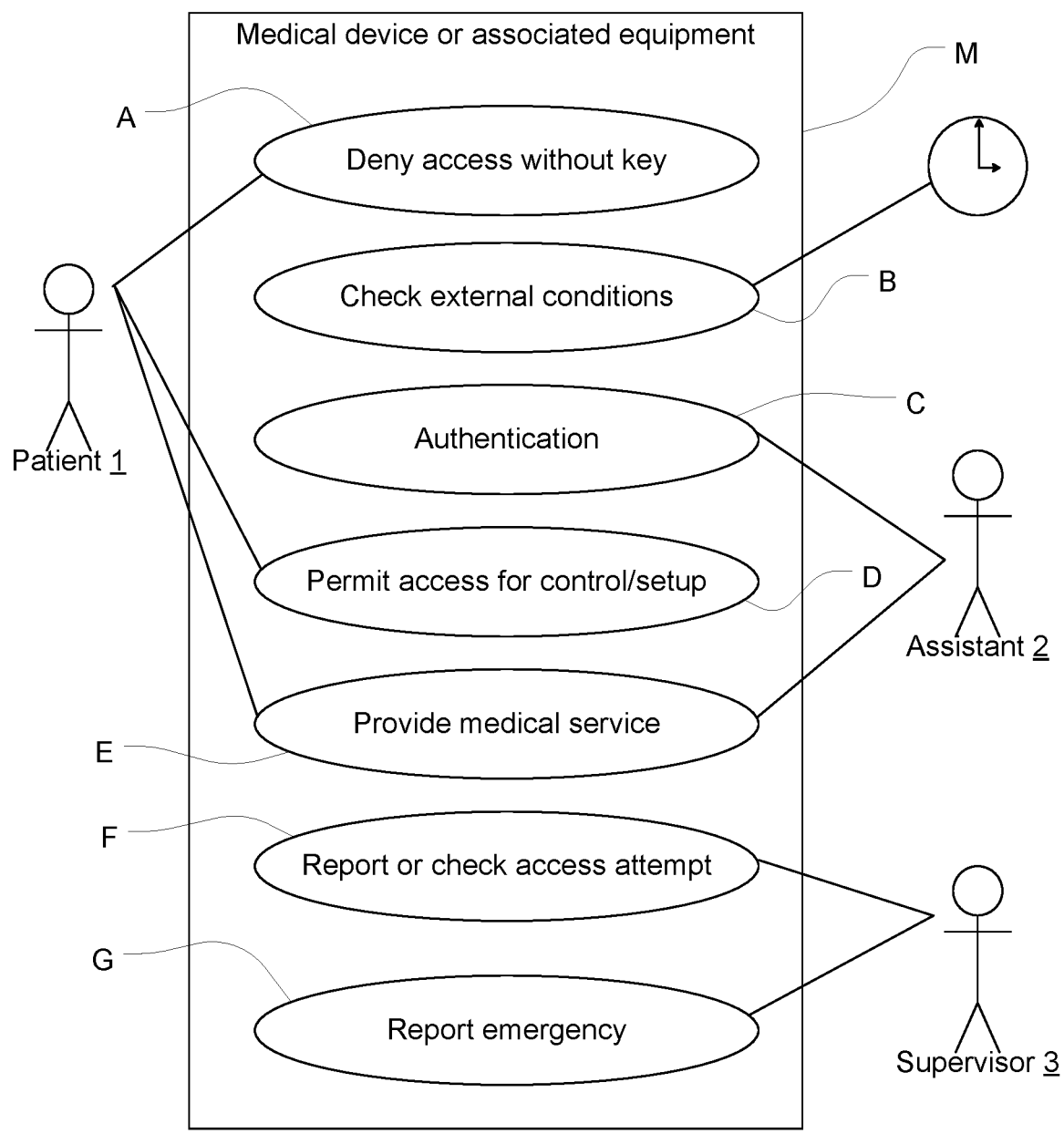
FIG. 2 is a flow chart illustrating a use case including human behavioral and state machine state changes.

Referring now to FIG. 2. the medical device 10, 50, &/or associated component(s) such as locker 55, indicated collectively at M, may be equipped as illustrated in the previous figures to perform the functions (use cases) indicated in FIG. 2. In embodiments, there are three individuals who may be involved: a patient 1; an assistant who is trained to monitor and also, possibly assist the patient 1 in using the medical device or associated component(s) M; and a supervisor, such as a medical doctor who has some responsibility with regard to the use of the medical device &/or associated component(s) M. The assistant 2 may be trained to provide emergency treatment or help in the set up of the equipment. In the ease of renal replacement therapy or chemotherapy, there may be a potential for serious adverse reactions including loss of consciousness. In embodiments, the assistant 2 would be present at a site where the medical device 10, 50 is used. The supervisor 3 may be charged with ensuring that a strict protocol is followed, such as a doctor, or may just be a second assistant. The supervisor may be at the site or remote from it.

A function A may be to prevent access by the patient 1 without the assistant 2 being present. In embodiments, the assistant 2 carries a key or, inherently, a biometric identifier such as his/her face. If the assistant 2 is not present, the medical device &/or associated component(s) M may be equipped, as discussed above, to deny access to the medical device &/or associated component(s) M. This prevents the patient 1 from using the medical device &/or associated component(s) M without assistance.

Another function B may be to check external conditions such as a time of day when use of the medical device &/or associated component(s) M is permitted or scheduled. This may provide an additional layer of protection against misuse. The medical device &/or associated component(s) M may check the external conditions, such as time of day, whether the assistant's training is current or expired, whether a prescription has been provided, or other separate criterion beyond the presence of the assistant. The presence of the assistance may be verified by another function C which is an authentication function. In the latter, the assistant may present his/her key or other indicia of identity and presence to unlock the medical device &/or associated component(s) M for use.

Another function D is to permit access to the medical device &/or associated component(s) M and, depending on the embodiment, including receiving and executing commands for control and setup as well as administering treatment or other service. Another function E is to provide services by the medical device &/or associated component(s) M.

Any improper use or proper attempt, to use the medical device &/or associated component(s) M may be reported by a function F to supervisor 3. For example, if the medical device &/or associated component(s) M detects a failure of authentication, it may report the event to the supervisor 3. The medical device &/or associated component(s) M may report every attempt, whether proper or improper, to the supervisor 3, and may also report to the assistant 2. In the latter case, if an authentication function C is executed without the assistant 2 being present, the assistant 2 may be notified by a communication to a remote terminal such as a cell phone. The latter situation could arise if the assistant 2 lost his/her key.

Note that the above use cases are not comprehensive nor is each function essential. Some benefits may be provided by a mechanically-locking cabinet configured to house the medical device &/or associated component(s) M, where the key is retained by the assistant. Another simple alternative for the medical device is for it to have a locking component.

Figure 3:
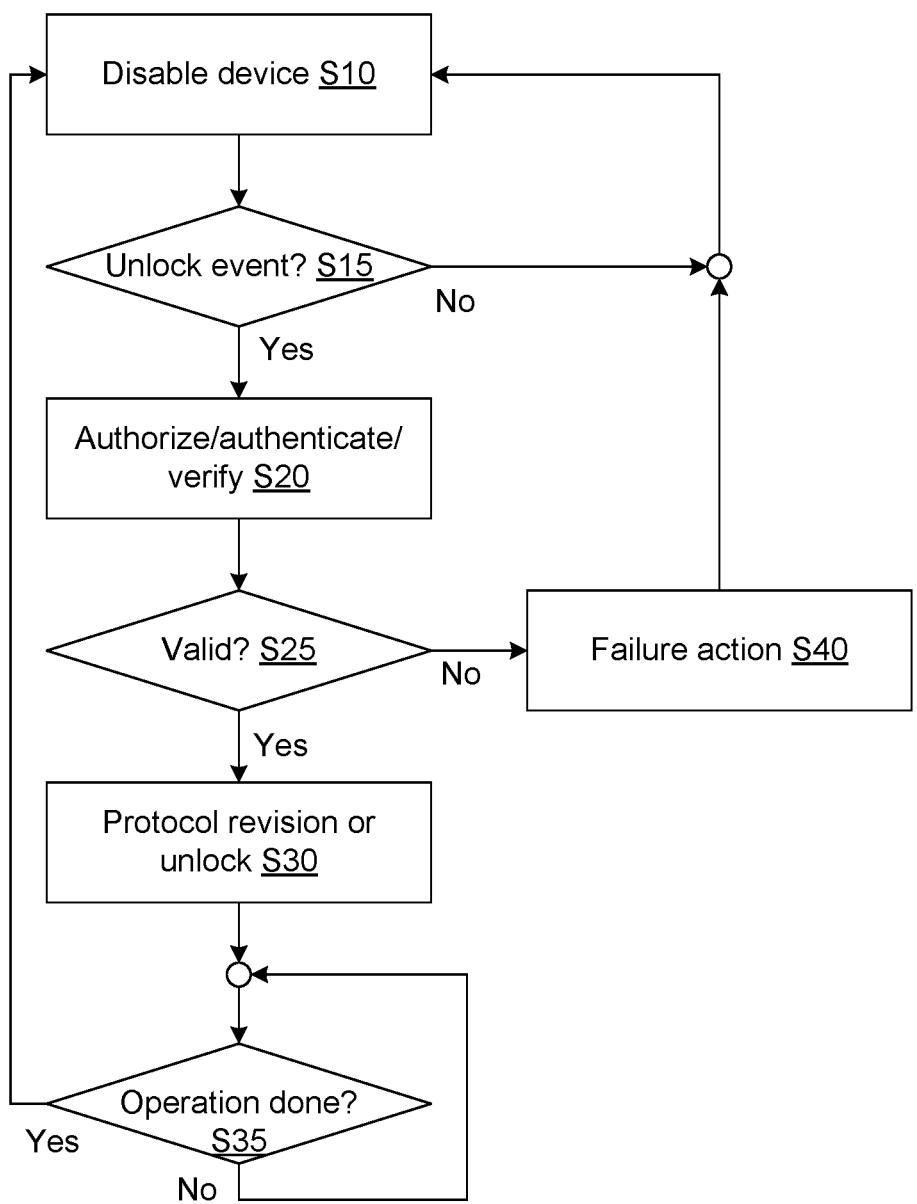
FIG. 3 is a flow chart illustrating an embodiment for controlling access or use of equipment or components for home medical treatment.

Referring now to FIG. 3, in a process that may be implemented by an attached controller (including controller 2) medical device 10 (50 or locker 55) may be disabled or rendered inaccessible respectively at step S10. Step 10 may represent a default condition. The disabling of the medical device may be provided through locking or lockable part 40. In step S15 an unlock event is detected, such as the entry of an authorization procedure implemented through a programmable processor in controller 2 or an attempt to connect smart card or memory device (embodiments of key/ID indicator 20). Here a user may be attempting to use the medical device 10 or 50 or access locker 55. If there is no unlock event at S15, then control returns to step S10. If there is, then an authorization process is performed at step S20. The authorization process may include verifying biometric indicia of identify, reading a smart card or other device including any of the devices identified with key/ID indicator 20.

Physically, what's going on so far in the process of FIG. 3 is that someone is attempting to gain access to the locker 55 or the medical device 10 or 50 to use it or obtain contents. In a preferred embodiment, the medical device or locker 10/50/55 is located at a patient's home and an assistant keeps the key/ID indicator 20 with him or her such that the patient cannot gain such access by him or herself. When the assistant or other authorized party is present, the assistant may complete the authorization process S20 and generate a valid condition (yes) at step S25.

In step S25, the validation process may verify that the key or identification indicia are present. This provide evidence that the assistant or authorized party is present such that access may be provided (to medical device 10, 50 or locker 55) in step S30. If a valid authorization is not completed in step S25, a failure action may be taken such as the display of a message on the user interface of the medical device or locker 10/50/55 or an output on any of the other I/O devices shown in FIGS. 1 and 2, such as a wireless message to a remote supervising party. The process may loop through step S35 until a treatment or other medical operation is performed, as appropriate, permitting the medical device 10/50 to returned to the default state S10. The latter step will loop through step S15 until an attempt is made to access supplies or equipment.

Step S20 may include using any type of key/ID indicator 20 or any action using I/O interface 15. For example, a username and/or password may be entered using the I/O interface 15 or a mechanical key may be used to unlock the lockable part 40, Also, step S30 may include enhancing services that are available through the medical device &/or associated component(s) M rather than simply enabling or disabling access. Step S40 may provide for remote notification such as an automated email or cell phone message. It may also include permanent logging of failures to authorize access.

Figure 4:
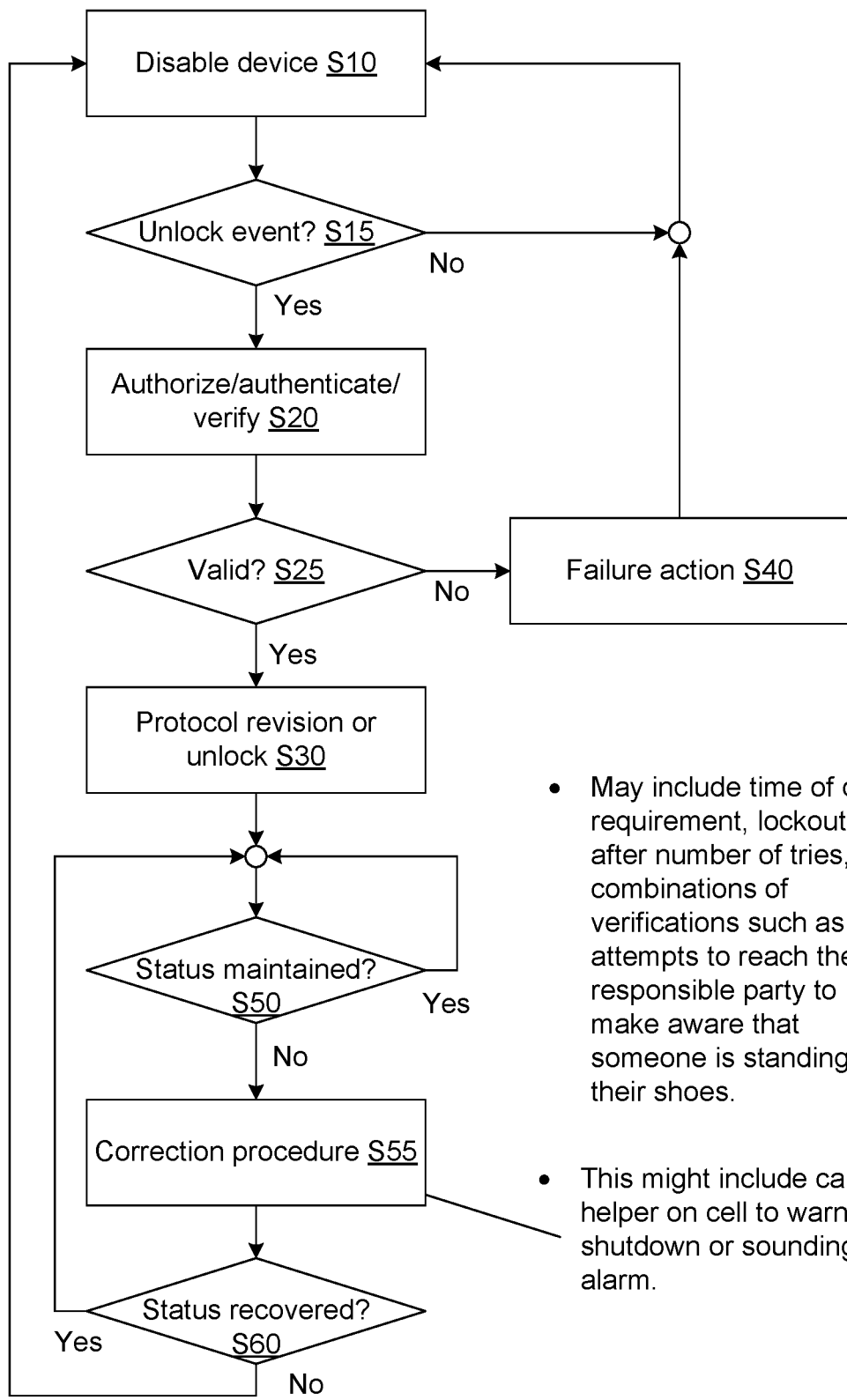
FIG. 4 is a flow chart illustrating a further embodiment for controlling access or use of equipment or components for home medical treatment.

Referring now to FIG. 4, two steps may be added to the procedure of FIG. 3 to check for the maintenance of a predefined status. For example, the predefined status may be that the assistant must remain, at least between intervals, present at the use location of the medical device &/or associated component(s) M. At step S50, it is determined if the status is not being maintained. If it is being maintained, control loops through step S50 until it is not. Then a correction procedure may be implemented at step S55 and if the status is recovered, control returns to step S50. If not, the medical device &/or associated component(s) M may be disabled or ameliorative response may be generated or automatically requested (not shown as a separate step) by the medical device &/or associated component(s) M.

Step S50 may correspond to one or more of the following, which are shown to provide illustrative examples and not to limit the embodiments in any way:

Prompting at predefined intervals through I/O interface 15 for confirmation of identity and presence of the assistant 2 by entering a password or voice command (with voice biometric identification).

Prompting at predefined intervals through I/O interface 15 for confirmation of identity and presence of assistant 2 by connecting a key/ID indicator 20.

Classifying a scene taken in by imaging device 35 to determine if the assistant 2 is still present, taking appropriate actions. Support for known techniques for this and other video classification concepts are shown in U.S. Pat. No. 6,611,206 for "Automatic system for monitoring independent person requiring occasional assistance;" U.S. Pat. No. 7,028,269 for "Multi-modal video target acquisition and re-direction system and method;" U.S. Pat. No. 6,931,596 for "Automatic positioning of display depending upon the viewer's location;" U.S. Pat. No. 6,925,197 for "Method and system for name-face/voice-role association;" U.S. Pat. No. 6,778,705 for "Classification of objects through model ensembles;" U.S. Pat. No. 6,714,594 for "Video content detection method and system leveraging data-compression constructs;" U.S. Pat. No. 5,561,718 for "Classifying faces;" U.S. Pat. No. 7,110,569 for "Video based detection of fall-down and other events;" U.S. Pat. No. 7,110,570 for "Application of human facial features recognition to automobile security and convenience;" US Application Publication Nos. 20060210112 for "Behavior recognition system;" 20060210958 for "Gesture training;" 20060204050 for "Face authenticating apparatus and entrance and exit management apparatus;" 20030128126 for "Method and apparatus for error warning with multiple alarm levels and types" and 20030128125 for "Method and apparatus for machine error detection by combining multiple sensor inputs" all of which are hereby incorporated by reference as if fully set forth in its entirety herein. (Note: The latter two applications describe mechanisms for observing a patient for safety reasons and illustrate a context in which video is captured of a treatment scene. This context is similar to what is described presently in the context of confirming the presence of the patient's helper. That is, these applications illustrate how a camera may be positioned to acquire the scene including a patient and a helper. They also illustrate response mechanism that may be used with the present embodiments.)

Classifying a scene taken in by imaging device 35 to determine the status of the patient, for example, if the patient's body temperature profile has changed to a predetermined pattern indicating imminent loss of consciousness, lack of blood flow or a pathological condition such as rapid or slow breathing. Support for known techniques for this may also be found in the above reference.

Step S55 may correspond to one or more of the following, which are shown to provide illustrative examples and not to limit the embodiments in any way:

Generating a wireless message or automated cell phone call to the assistant 2.

Generating a wireless message or automated cell phone call to the supervisor 3.

Generating an alarm.

Changing the operational regime of the medical device 10, 50 to a safe mode.

Note that step S60 may include returning the medical device 10, 50 to a normal operating mode. If the operating mode is changed, or performing a function to disable an alarm or respond to a message.

Figure 5:
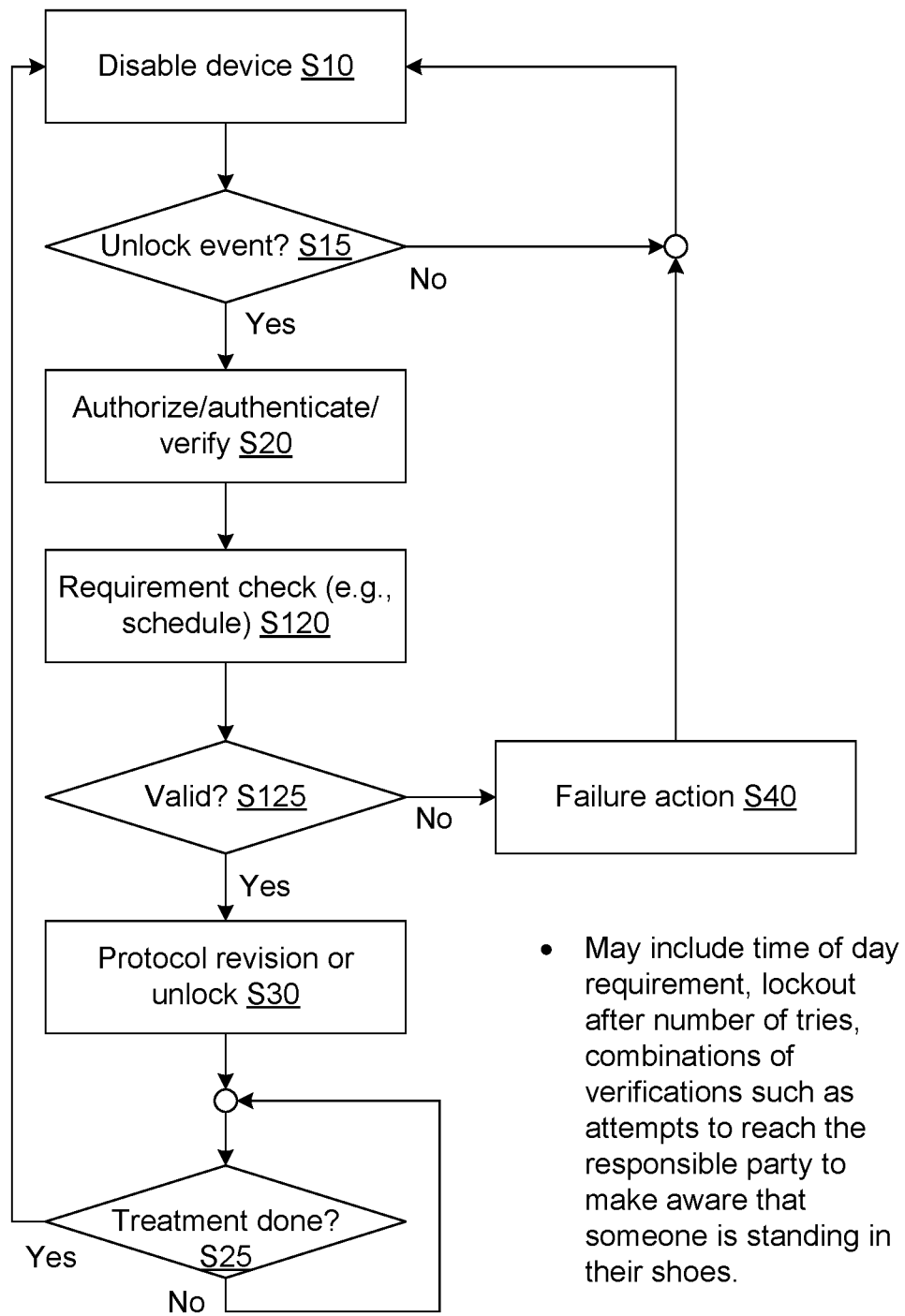
FIG. 5 is a flow chart illustrating a further embodiment for controlling access or use of equipment or components for home medical treatment.

Referring now to FIG. 5, a step S120 is added to the flow of FIG. 3 for verifying some external condition in addition to the authentication process. This may be for example, checking that the current time and date are correct for use of the medical device &/or associated component(s) M. It may include checking an internally stored prescription for currency. It may include checking the status of the training or training level of the assistant. The latter may include checking a database stored on the server 56 which stores the assistant's identification in relation to training level and comparing to a predefined protocol also stored on the server 56.

Figure 6:
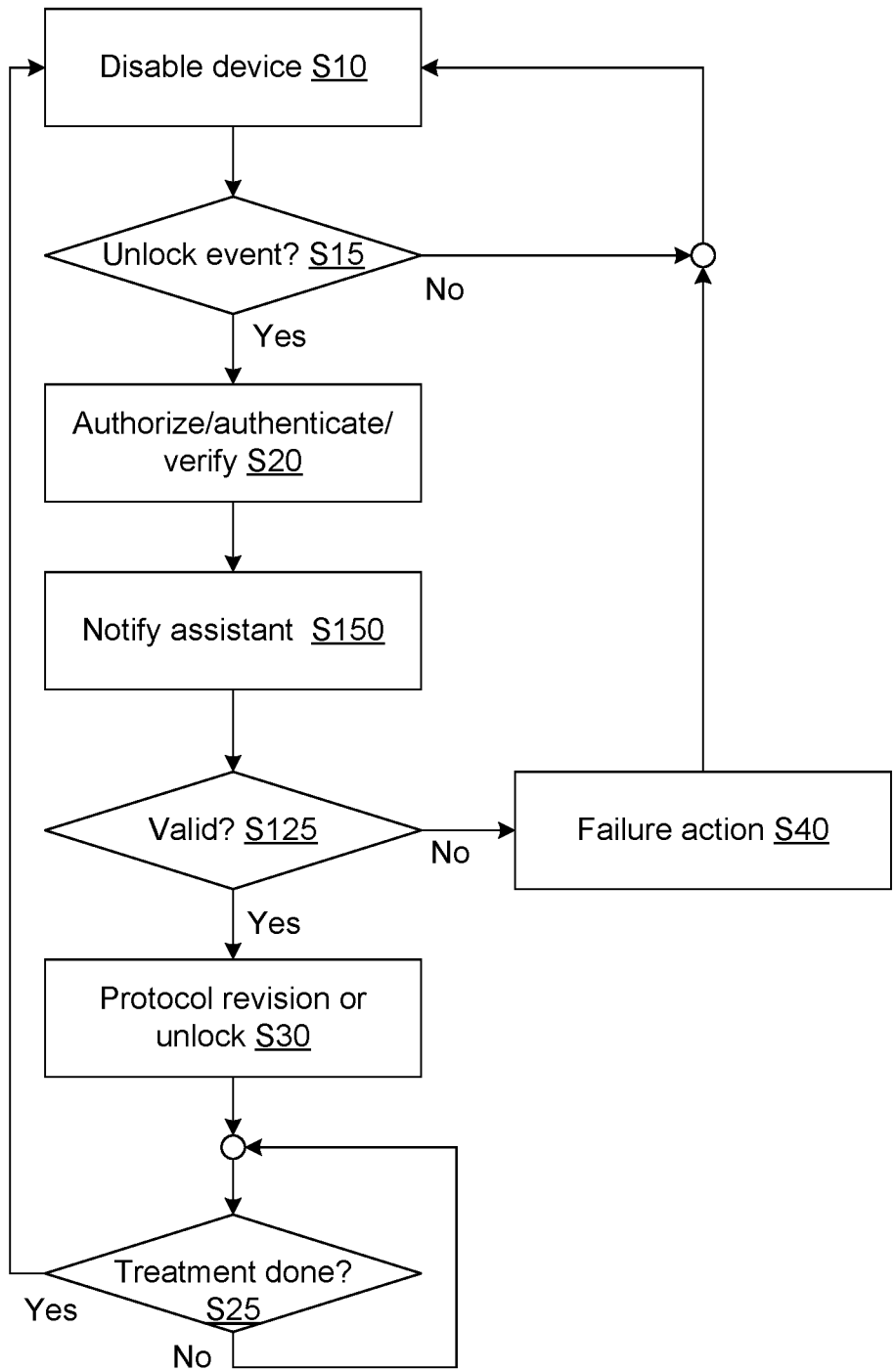
FIG. 6 is a flowchart illustrating a further embodiment for controlling access or use of equipment or components for home medical treatment.

Referring to FIG. 6, a step S150 may be added which includes generating a notification, such as by cell phone, email, instant message, SMS message, POT call, or other means to notify the assistant that his or her key is being used to authenticate in step S20. For example, if the assistant lost his/her key, the notification would provide the assistant the ability to take some action if the assistant were not actually present. Step S125 may include waiting for an additional time for an action to be taken in response to the step of S150.

Although the present invention has been described herein with reference to a specific preferred embodiment, many modifications and variations therein will be readily occurring to those skilled in the art. Accordingly, all such variations and modifications are included within the intended scope of the present invention as defined by the following claims.

The invention claimed is:

1. A dialysis treatment device that is used during a treatment session at a first location, the dialysis treatment device comprising:
    a medical treatment component that performs at least one of hemodialysis, hemofiltration, and peritoneal dialysis on a patient during the treatment session at the first location; and
    a monitoring system that receives data from one or more sensors connected to the monitoring system,
    wherein:
    the medical treatment component includes a controller connected to the Internet and communicating with information servers, the controller controlling functions of the medical treatment component and directly obtaining instructions from the information servers through the communicating with the information servers,
    the dialysis treatment device further comprises a user interface adapted for permitting an operator to control the functions of the medical treatment component, and
    the medical treatment component includes a data storage for storing an internal representation of a prescription for treatment of the patient,
    the controller reports a use of the medical treatment component to a remote supervisor by said Internet or remote terminals, and sends a message to the remote supervisor by said Internet,
    the monitoring system performs a presence confirmation at predefined time intervals during the treatment session to confirm a presence of an authorized helper at the first location, the authorized helper being different from the patient, by automatically and at the predefined time intervals during the treatment session, generating one or more verification request signals requesting a helper to manually input a verification response into the user interface of the monitoring system in response to the one or more verification request signals, the verification response verifying that the helper is present at the first location, and identifying that the helper is the authorized helper, and confirming a pattern of presences of the authorized helper over a plurality of said predefined time intervals during said treatment session in which said medical treatment component is operative to deliver therapy to the patient based on said verifying and identifying; and
    the monitoring system generates a signal indicative of an abnormal condition when the pattern of the presences of the authorized helper is not confirmed during said treatment session and causing the medical treatment component to go into a failsafe operational mode to reduce risks to the patient during said treatment session.

2. The dialysis treatment device of claim 1, wherein the monitoring system includes a video camera and a video classification engine that monitors a scene that includes the patient and the helper to confirm that the helper is present at the first location and is the authorized helper.

3. The dialysis treatment device of claim 1, wherein the one or more sensors include an authentication device including at least one of a key code receiver, an RFID reader, mechanical lock, a biometric reader, a magnetic stripe reader, a nonvolatile memory card reader, a smart card reader, a video camera, or a bar code reader.

4. The dialysis treatment device of claim 1, wherein the monitoring system generates an alert signal in response to the abnormal condition.

5. The dialysis treatment device of claim 1, wherein the monitoring system generates an alert signal and waits for a reception of an alert-cancel command after generating the alert signal, the monitoring system causing the medical treatment component to go into the failsafe operational mode in response to the abnormal condition and a failure of an alert-cancel signal command being received.

6. A method for controlling an extracorporeal blood treatment machine during a treatment session at a first location to reduce a risk of continuing a blood treatment procedure of a patient in an absence of an authorized helper other than the patient in an immediate vicinity of the extracorporeal blood treatment machine, comprising:

providing the extracorporeal blood treatment machine at the first location, the extracorporeal blood treatment machine having controller to control medical treatment functions of the extracorporeal blood treatment machine and connected to the Internet and communicating with information servers at a second location remote from the first location;

obtaining instructions by the controller from the information servers, through the communicating with the information servers, the instructions including at least prescription information specific to the patient at the first location;

reporting a status and/or notifying of conditions of the extracorporeal blood treatment machine by the controller to the information servers at the second location;

receiving the instructions at a user interface of the extracorporeal blood treatment machine to control the medical treatment functions of the extracorporeal blood treatment machine;

performing, by the extracorporeal blood treatment machine, presence confirmation at predetermined time intervals during the treatment session and after starting the treatment session, to confirm a presence of the authorized helper at the first location, the authorized helper being different from the patient, the performing of the presence confirmation including automatically generating one or more verification request signals requesting a helper to manually input a verification response into the user interface of a monitoring system of the extracorporeal blood treatment machine in response to the one or more verification request signals, the verification response verifying that the helper is present at the first location, and identifying that the helper is the authorized helper, and confirming a pattern of presences of the authorized helper over a plurality of the predetermined time intervals during the treatment session in which the extracorporeal blood treatment machine is operative to deliver therapy to the patient based on the verifying and identifying; and generating a signal indicative of an abnormal condition when the pattern of the presences of the authorized helper is not confirmed and causing the extracorporeal blood treatment machine to go into a failsafe operational mode to reduce risks to the patient during the treatment session; and sending, by the controller via said Internet, a message to a remote supervisor responsively to the presence confirmation failing to confirm the presence of the authorized helper at the first location during said treatment session.

7. The method according to claim 6, wherein the status includes notifications requiring special or immediate attention and to transmit information and receive commands to/from the information servers.

8. The method according to claim 6, wherein the performing of the presence confirmation further comprises:

(1) responsively to a receipt and the confirmation of the input of the verification response effective to confirm the presence of the helper at the first location and confirm an identity of the helper as the identity of the authorized helper, continuing a normal blood treatment process by the extracorporeal blood treatment machine; and (2) responsively to any absence of the receipt and the confirmation of the input of the verification response effective to confirm the presence of the helper at the first location and confirm the identity of the helper as the identity of the authorized helper, implementing the failsafe operational mode which includes discontinuing the normal blood treatment process to cause the extracorporeal blood treatment machine to go into the failsafe operational mode to reduce the risks to said patient during said blood treatment procedure; and continuing the generating the one or more verification request signals, by the extracorporeal blood treatment machine, for the input at the predetermined time intervals to receive a subsequent input entered by the authorized helper into the user interface of the extracorporeal blood treatment machine throughout the blood treatment procedure until the blood treatment procedure is complete or the absence of the receipt and the confirmation of the subsequent input is determined, wherein the subsequent input is of a type that requires an action by the helper such that the identity and the presence of the helper are confirmed.

9. The method of claim 8, wherein the subsequent input includes a manual entry through the user interface of the extracorporeal blood treatment machine that requires a physical presence of the authorized helper.

10. The method of claim 8, wherein the subsequent input includes bio-authentication input through the user interface of the extracorporeal blood treatment machine that requires a physical presence of the authorized helper.

11. The method of claim 8, wherein the subsequent input includes authenticating the identity of the authorized helper to ensure the helper is the authorized helper.

12. The method of claim 8, wherein the blood treatment procedure is a renal replacement therapy.

13. The method of claim 8, wherein the implementing said failsafe operational mode includes clamping blood lines of the extracorporeal blood treatment machine.

14. The method of claim 8, wherein the implementing said failsafe operational mode includes generating one of an automated cellular message and an automated telephonic message to an ambulance service.

15. The method of claim 8, wherein the implementing said failsafe operational mode includes slowing a pumping rate through blood lines of the extracorporeal blood treatment machine or terminating said blood treatment procedure.

16. The method of claim 8, wherein said extracorporeal blood processing machine performs a warning procedure responsively to said absence of the receipt and the confirmation of said subsequent input, said warning procedure including generating a first notification signal to indicate that the failsafe operational mode will be implemented within a predefined time if the subsequent input is not received within the predefined time, and controlling said extracorporeal blood treatment machine to implement the failsafe operational mode responsively to a lapse of the predefined time.

17. The method of claim 8, wherein the subsequent input is applied using a direct input/output interface including one of a keyboard, keypad, speech interface, touchscreen, or a mechanical interface.

18. The method of claim 8, wherein the receiving the subsequent input includes authenticating the authorized helper at least three times during the blood treatment procedure, the at least three times being spaced apart such that a third time is more than half-way through the blood treatment procedure.

\* \* \* \* \*